United States Patent [19]

Davies et al.

[11] Patent Number: 4,505,269
[45] Date of Patent: Mar. 19, 1985

[54] ANKLE SPLINT

[76] Inventors: John R. Davies; Glen V. Rice, both of 1206 N. 199th, Seattle, Wash. 98133

[21] Appl. No.: 515,771

[22] Filed: Jul. 21, 1983

[51] Int. Cl.³ .............................................. A61F 5/04
[52] U.S. Cl. .................................................. 128/87 R
[58] Field of Search ................... 128/87 R, 89 R, 90, 128/83, 84 A, 85, 83.5, 80 H

[56] References Cited

U.S. PATENT DOCUMENTS

| D. 272,281 | 1/1984 | Alush | 128/89 R X |
|---|---|---|---|
| 3,584,402 | 6/1971 | Silverman | 128/83.5 X |
| 3,800,789 | 4/1974 | Schloss | 128/90 |
| 4,177,583 | 12/1979 | Chapman | 128/83.5 X |
| 4,217,893 | 8/1980 | Payton | 128/89 R |
| 4,289,122 | 9/1981 | Mason et al. | 128/89 R X |
| 4,414,965 | 11/1983 | Mauldin et al. | 128/87 R |
| 4,454,871 | 6/1984 | Mann et al. | 128/89 R X |

Primary Examiner—William H. Grieb
Attorney, Agent, or Firm—Christensen, O'Connor, Johnson & Kindness

[57] ABSTRACT

A walking splint for substantially immobilizing the ankle joint of a human includes four discrete members that are adapted for placement on the posterior, lateral, medial and anterior portions of the lower leg and foot to substantially encase the ankle joint. The members conform closely to the anatomical features of the lower leg and foot and include an inner layer of compressible foam material to enable a snug fit over a range of sizes of leg and foot. The members are held in place by a plurality of spaced, adjustable straps that encircle the members. The posterior member of the splint extends to underlie the foot and holds the foot in a constant right angular relation to the leg. The portion of the posterior member underlying the foot includes an integrally formed arch support and, preferably, the exterior surface of the underlying portion comprises an antiskid surface. The lateral and medial members are formed with outwardly flared distal portions covering the respective malleoli, and the distal portions include recesses to accommodate the bony prominences of the malleoli.

13 Claims, 11 Drawing Figures

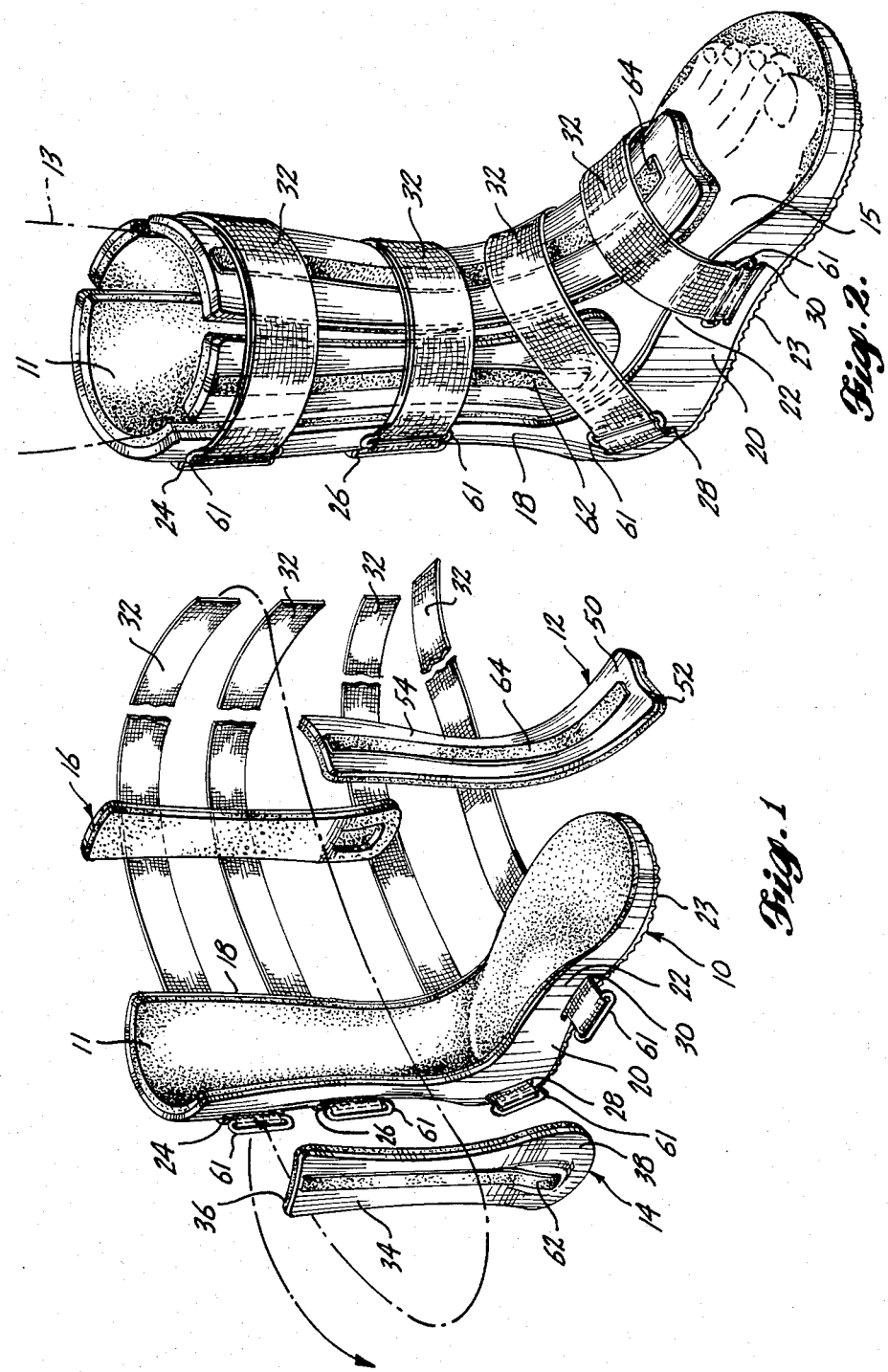

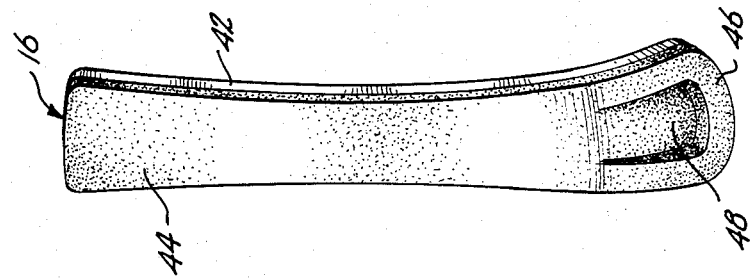
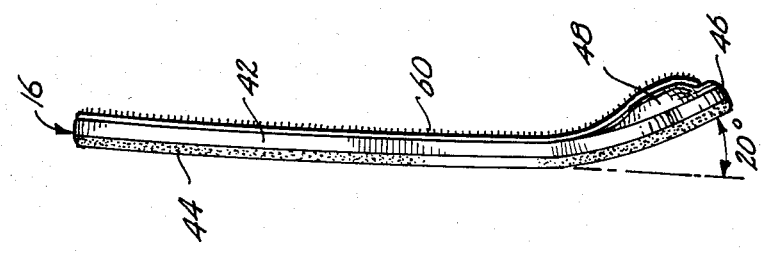
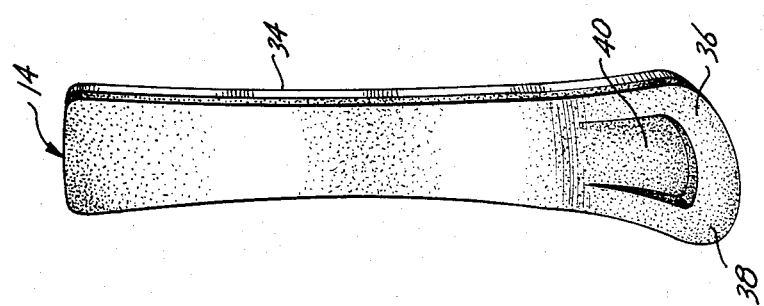
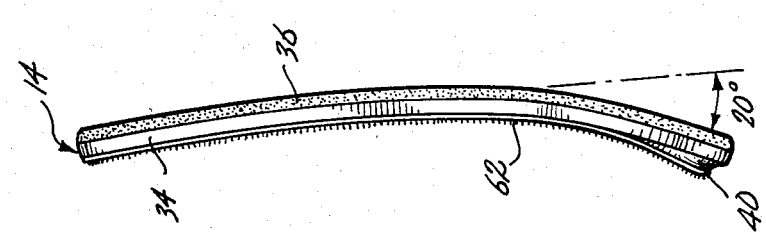

ANKLE SPLINT

BACKGROUND OF THE INVENTION

This invention relates to orthopedic appliances and more specifically relates to removable appliances for substantially immobilizing the ankle joint. One of the most common orthopedic injuries is the ankle sprain. This injury occurs when there is sudden forceful hyperinversion or hypereversion of the ankle joint. The ligaments connecting the ankle bones (malleoli) to the foot are thus partially or completely torn. There is immediate pain and inability to bear weight on the affected limb. Swelling then occurs at the site of the injury, generally in proportion to its severity.

Treatment objectives are to relieve pain and to promote healing of the torn fibers of the involved ligaments. These objectives are accomplished by immobilization of the affected joint in a neutral position and reduction of the distortion of the joint due to swelling. Elevation, compression and cold applications, initially, followed by alternating cold and warm baths later in the course of treatment, are valuable adjuncts.

Immobilization is accomplished by a variety of methods. One method is to wrap an elastic bandage around the foot and ankle, occasionally incorporating U-shaped felt pads that are placed so that the soft tissue surrounding the malleolus is compressed to minimize swelling. Crutches are used for partial weight bearing for several days or weeks. The elastic bandage does not afford the complete immobilization needed for solid healing of severely torn ligaments and its use is associated with a higher incidence of reinjury. Daily activities are limited by the associated use of crutches.

A second method of immobilization is the application of a plaster cast with the addition of a walking heel or boot. Plaster casts permit firm immobilization, but require a two- or three-day period of walking with crutches, using extreme care not to bear weight on the cast because to do so causes it to soften, rendering it useless. Since these casts usually stay on for at least two weeks before they are removed and/or replaced, they cause itching and sometimes dermatitis secondary to perspiration and bacterial overgrowth. As tissue swelling about the ankle decreases and muscle atrophy occurs in the calf, the cast becomes loose and uncomfortable. Thus, the extremity should be recasted, entailing more physician time and expense and another period of crutch usage.

Another method of treatment involves the application to the ankle of various preformed apparatus, such as braces and nonplaster casts. In spite of some apparent advantages, none of these appliances has ever gained popular acceptance. It is suspected that one reason for the lack of acceptance is the failure of the appliance to account for the bilaterality of the extremities, i.e., left and right sides. When one observes the foot and ankle it is is apparent that there are marked differences between the medial and lateral aspects. First of all, the medial side is larger. Secondly, the first metatarsophalangeal joint is located anteriorly to the fifth metatarsophalangeal joint and is more prominent. Thirdly, there is an arch located on the medial aspect of the foot but none on the lateral aspect. Fourthly, the medial malleolus is located anteriorly and superiorly to the lateral malleolus. The foregoing anatomical facts would seem to preclude a comfortable fit by any snug fitting cast or apparatus that encases the foot and ankle but does not incorporate at least some features of bilaterality into its design.

In addition, it is noted that the prior art appliances typically apply pressure evenly over the entire ankle without consideration that there should be less pressure over the bony prominences (malleoli) and greater pressure over the surrounding soft tissue in order to reduce swelling around the torn ligaments.

It is therefore an object of the present invention to provide a splint for immobilizing the ankle joint that is capable of being worn comfortably for two to eight weeks, depending on the severity of the sprain, to ensure complete ligamentous healing.

It is a further object of this invention to provide such a splint that allows early ambulation without the use of crutches so that little time is lost from work, school, or other activities and that incorporates a walking surface as an integral part of the unit.

It is another object of the invention to provide a splint that is easily applied, easily removed for bathing, rest and physical therapy and is easily reapplied.

It is also an object of the invention to provide a splint that is adjustable to accommodate tissue swelling and muscle atrophy as well as individual variations in anatomy and that, once adjusted, stays firmly in place.

Still another object of the invention is to provide a splint that can be produced for both left and right lower extremities and takes into account the anatomical differences between the medial and lateral aspects of the ankle joint as well as preventing pressure directly on the malleoli while applying increased pressure over the peri-malleolar tissue to decrease edema and thereby promote healing of torn ligaments.

SUMMARY OF THE INVENTION

A walking ankle splint is hereby presented for the treatment of ankle sprain, which is designed to provide stability and immobilization of the ankle joint while said sprained ankle ligaments are healing. The splint includes four substantially rigid plastic members, each lined with a compressible material. A posterior member supports the back of the leg, extends around the underside of the foot, and provides a walking platform with an arch support and an antiskid undersurface. Medial and lateral members support the respective sides of the lower leg and ankle bones and are formed with distal outward flares and compatible recesses to anatomically conform to the lower leg and ankle bones. An anterior member supports the anterior portion of the lower leg and upper foot. The four members are held in place encasing the ankle joint by a plurality of straps with adjustable fasteners so that the members are held snugly in place. The straps allow removal or adjustment and reapplication of the splint members. Preferably, the straps are anchored within the posterior member and have an attached rectangular ring that acts as a buckle and also prevents circumferential slippage of the straps. Preferably, the straps are secured to the side and anterior components by attached, easily removable fastening means such as hook-and-loop fasteners of the type sold under the trademark VELCRO to permit multidirectional adjustment of the splint members. In the preferred embodiment, the splint members are made in a plurality of sizes and for both the left and right lower extremities.

BRIEF DESCRIPTION OF THE DRAWINGS

The ankle splint of the present invention will be better understood by those of ordinary skill and others upon reading the ensuing specification when taken in conjunction with the accompanying drawings wherein:

FIG. 1 is an exploded isometric view of one embodiment of a splint made in accordance with the principles of the present invention ready to be applied to the left lower extremity;

FIG. 2 is an isometric view of the splint of FIG. 1 secured in place on the left lower extremity;

FIG. 6A is a front elevational view of the medial member of the splint of FIG. 1 for the left lower extremity;

FIG. 6B is a side elevational view of the medial member of the splint of FIG. 1;

FIG. 7A is a front elevational view of the lateral member of the splint of FIG. 1 for the left lower extremity;

FIG. 7B is a side elevational view of the lateral member of the splint of FIG. 1;

DETAILED DESCRIPTION OF THE PREFERRED EMBODIMENT

Figure 5:
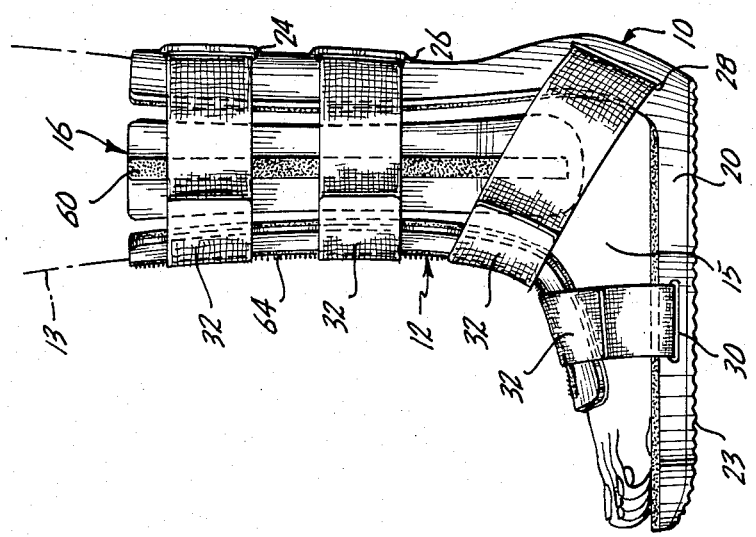
FIG. 5 is a side elevational view of the splint of FIG. 1 in place on the left lower extremity from the lateral aspect.

FIG. 1 illustrates a preferred embodiment of an ankle splint made in accordance with the principles of the present invention. The splint comprises a posterior member 10, an anterior member 12, a medial member 14, and a lateral member 16. The members are formed so that they encompass and hold firm the lower leg and foot of the patient to substantially immobilize the ankle joint during healing of an ankle sprain. The splint, in its assembled state, positioned on a lower leg 13 and foot 15 of a person is shown in FIGS. 2, 3, 4 and 5.

The posterior member 10 is the largest component of the splint. The posterior member is generally L-shaped and includes a vertical portion 18 that supports the posterior aspect of the leg from approximately the midcalf of the leg downwardly to the heel. The posterior member wraps around the heel to provide an underlying platform portion 20 upon which the foot of the patient rests. The vertical portion 18 is typically comprised of an outer plastic shell that is approximately 0.3 centimeters thick at the proximal (upper) end and gradually becomes thicker (approximately 1.0 centimeters) over the Achilles tendon aspect where more support is needed. The vertical portion 18 and the platform portion 20 of the posterior member 10 form substantially a right angle. The posterior member has a heel recess formed therein to accommodate the heel of the wearer. The heel recess is typically approximately 7.5 centimeters at its widest diameter for an adult splint. (Unless specified all further dimensions will be given for a size of splint that will fit an average adult male.) Typically the plastic foot platform portion 20 is approximately 2.5 centimeters thick except for the medial aspect in which it becomes gradually thicker under the arch of the foot to create an arch support portion 22. The maximum thickness of the arch support portion 22 is approximately 5.0 centimeters.

Figure 3:
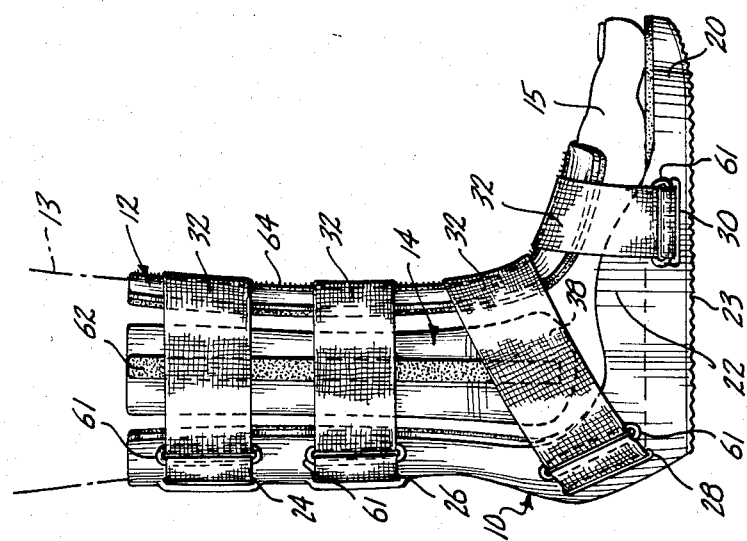
FIG. 3 is a side elevational view of the splint of FIG. 1 in place on the left lower extremity from the medial aspect.

The undersurface 23 of the foot platform portion 20 of the posterior member 10 preferably has a plurality of spaced grooves formed therein to increase the traction of the surface and minimize the possibility of slipping while walking. The grooves are best seen in FIGS. 3 and 5. Alternatively, a separate walking surface of rubber or some other antiskid material can be affixed to the underside of the posterior member. The posterior member has integrally formed in it four slots 24, 26, 28 and 30 for the purpose of retaining four straps 32 that encircle the members to hold them in their correct positions about the lower extremity. The slots 24 and 26 are formed in the vertical portion 18 of the posterior member while the slot 30 is formed in the foot platform portion 20 approximately under the center of the foot. The fourth slot 28 is formed in a portion of the posterior member behind the heel of the wearer at approximately the place where the vertical portion 18 and foot platform portion 20 meet. Typically, the slots have inside dimensions of approximately 5.0 centimeters by 0.5 centimeters to snugly contain a portion of the fastener straps 32 which pass through the slots. The entire inner surface of the posterior member 10 is lined with a layer 11 of compressible foam. The foam conforms more comfortably to the immobilized lower extremity than the hard plastic shell of the posterior member. The compressed foam in the preferred embodiment described herein is approximately 1.0 centimeters thick.

Referring to FIGS. 6A and 6B, a preferred embodiment of the medial member 14 is shown. The medial member 14 consists of an outer shell 34 of semi-rigid plastic material and an inner layer 36 of compressible foam material. As viewed from the medial aspect as shown in FIG. 6B, the medial member 14 has a substantially rectangular, elongated shape with a rounded distal portion 38 adapted to overlie the malleolus. The distal portion 38 has a slight anterior projection to conform to the adjacent posterior and anterior members when the splint is in place on the lower extremity and foot of the patient. In FIG. 6A, it can be seen that the medial member has an outward flare of the distal portion 38 with respect to the remaining elongate portion of the medial member of approximately 20 degrees to anatomically conform to the shape of the lower extremity.

Two well-known physiological principles state that prolonged pressure over bony prominences may result in pressure sores and that edema (excess tissue fluid) retards healing. In keeping with these principles, there is a recessed area 40 formed in the distal portion 30 of the medial member to correspond and conform to the anatomic configuration of the medial malleolus thereby decreasing pressure over the bony prominence of the medial malleolus and concurrently allowing greater pressure to be applied over the edematous peri-malleolar tissues. In the illustrated embodiment, intended for use by an average sized adult male, the recessed area 40 is approximately 4.0 centimeters at the widest anteroposterior diameter on the compressed foam material aspect.

FIGS. 7A and 7B illustrate a preferred embodiment of the lateral member 16 that comprises an outer shell 42 of semi-rigid plastic material and an inner layer 44 of compressible foam material. In both medial and lateral members typically, the outer shell is approximately 0.3 centimeters thick while the compressible foam layer is approximately 1.0 centimeters thick. As viewed from the lateral aspect shown in FIG. 7B, the lateral member 16 has a generally rectangular shape with a rounded distal portion 46 that overlies the lateral malleolus when the splint is in place on the lower extremity of the patient. For an average adult male the lateral member 16 is typically approximately 30 centimeters long and 4.5 centimeters wide in the central portion.

As viewed from the anterior aspect shown in FIG. 7A, the distal portion 46 is flared outwardly approximately 20 degrees with respect to the elongate portion of the lateral member to conform to the anatomical configuration of the lateral aspect of the lower extremity. In conformance with the previously stated physiological principles relating to edema and pressure sores, there is a recessed area 48 formed in the distal portion 46 of the lateral member to correspond and conform to the anatomic configuration of the lateral malleolus, thereby decreasing pressure over the bony prominence of the lateral malleolus and allowing greater pressure to be applied over the peri-malleolar tissues surrounding the malleolus, thereby diminishing the possibility of edema. Again, for the average adult male the recessed area 48 is approximately 3.0 centimeter at the widest anteroposterior diameter on the compressed foam material aspect. Note that the recessed portion 48 of the lateral member 16 is slightly smaller than the recessed portion 40 of the medial member 14. This again takes into consideration the anatomical makeup of the typical lower extremity.

As can be seen in FIGS. 2 through 5, the anterior member 12 covers the anterior portion of the lower leg and a portion of the dorsum of the foot. It is positioned between the medial and lateral members 14 and 16. The anterior member consists of a plastic outer shell 50 and an inner compressible foam layer 52. The anterior member 12 is formed in such a fashion as to conform to the anatomical configuration of the lower extremity. The proximal (upper) portion 54 is of a height equal to the lateral, medial and posterior members, and for a typical adult male it is approximately 7.5 centimeters at its widest point. As the anterior member descends toward the ankle, it narrows to accommodate the typical narrowing of the leg and, again, for a typical adult male narrows to approximately 4.5 centimeters. The anterior member then flares out again over the dorsum of the foot where it is formed in a convex manner with the apex of the convexity overlying the first metatarsal bone. The flared portion of the anterior member 12 overlies the proximal portion of the metatarsal bones and the general anatomical conformity allows a snug fit to be obtained between the anterior member 12 and the foot 15. The flared portion of the anterior member stops short of covering the metatarsophalangeal joint because wide individual anatomical disparities caused by bunions, callouses, etc., preclude a uniformly comfortable fit. In addition, to achieve immobilization of the ankle, it is unnecessary to immobilize the metatarsophalangeal joints. The anterior member 12 comprises an outer shell 51 of semi-rigid plastic material and is lined with a layer 53 of compressible foam material.

Figure 4:
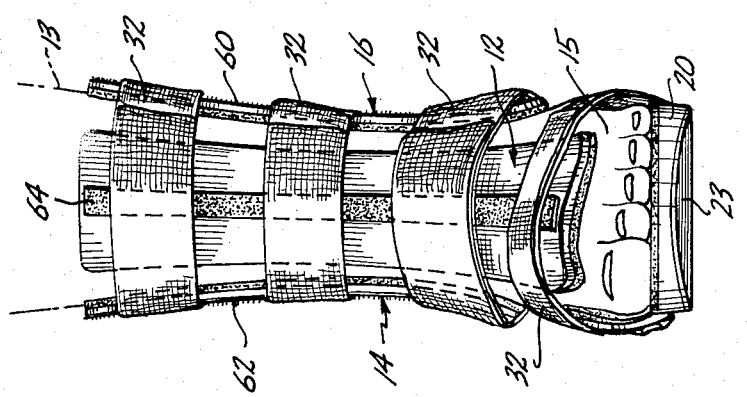
FIG. 4 is a front elevational view of the splint of FIG. 1 in place on the left lower extremity.
Figure 8:
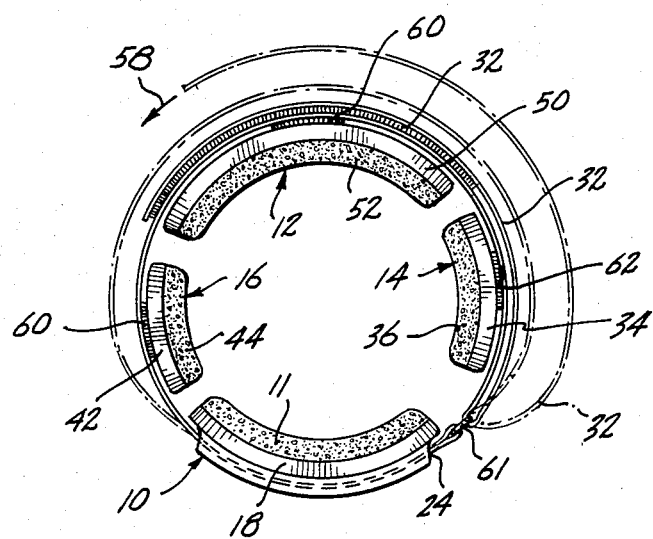
FIG. 8 is a plan view of the splint of FIG. 1 for the left lower extremity in the assembled condition.
Figure 9:
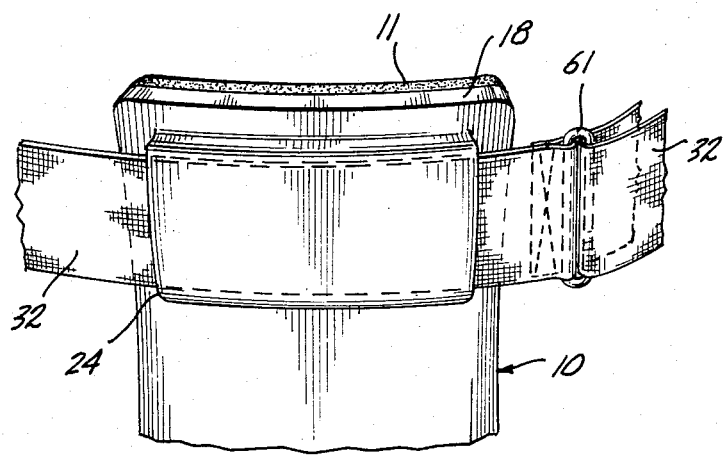
FIG. 9 is a detailed view in expanded scale of a portion of the posterior member of the splint of FIG. 1 for the left lower extremity.

The fastener straps 32 are used to hold the lateral, medial, anterior and posterior members in place, securely positioned about the lower extremity. The straps 32 are secured by passing through the previously described retainer slots 24, 26, 28 and 30 formed in the posterior member 10. Typically, the straps are approximately 5.0 centimeters wide and are made of a durable fabric material. FIGS. 3, 4 and 5 show, from various views, the use of the straps 32 in holding the members securely to the lower extremity of the patient as the splint is used to immobilize the ankle joint. Each of the fastener straps, as viewed in FIG. 8, wraps completely around the four members and passes through a rectangular ring 61 affixed to a first end of the strap. The strap is then looped back as illustrated by the arrow 58 in the opposing direction so it can be pulled tight and the end of the strap secured to keep the splint in place. FIG. 9 illustrates in greater detail how the strap 32 passes through one of the retainer slots 24 and loops through the rectangular ring 61. In the preferred embodiment, the straps 32 are made of a loop fastener component material such as used in combination with a hook fastener component material to form the hook and loop fastening system such as that sold under the trade name VELCRO. A second end of the strap has a piece of the hook fastener component affixed to it and the second end can therefore be attached to the body of the strap when the strap is pulled tight. Use of such hook and loop fastening means, as opposed to a simple buckle, provides for continuous adjustability range for the strap to conform to the wide range of sizes of patients. Therefore, patients within a range of sizes can use the same splint and a separate customized splint does not have to be made for each individual patient. This lowers substantially the cost involved in the use of the ankle splint of the present invention.

The lateral, medial and anterior members each have a respective strip 60, 62 and 64, respectively, of the hook component of the fastening material affixed to approximately the midline of the longitudinal axis of each of the respective plastic outer shells. Since the strap itself is comprised of the loop component material of the hook and loop fastener system, the strips 60, 62, and 64 attached to the lateral, medial and anterior members will adhere to the strips of material to provide multidirectional position adjustment and to assist in holding the lateral and medial members in place vertically on the lower extremity and, also holding the anterior member in place firmly against the dorsum of the foot of the patient. The rectangular rings 61 are of a size large enough to prevent their passing through the slots in the posterior member. The end of the fastener straps loop through the rectangular rings and then double back and secure upon themselves by means of the hook and loop fastening characteristics. If one considers the rings in the sense of pulleys, in accordance with physical principles, the mechanical advantage obtained by pulling the strap against the ring to apply more tension in tightening the straps provides a more firm fit of the splint to the leg. The make-up of the various straps 32 and strips 60, 62 and 64 can either be hook or loop components of the fastening system as long as the two comprise a cooperative pair to enable the strap to adhere to the respective strips.

In the biological world, animals have bilateral extremities, one extremity being the mirror image of the other. For this reason, a well fitting glove cannot fit both hands, a well fitting shoe cannot fit both feet, and a well designed ankle splint cannot fit both ankles. It is therefore necessary, because of the bilaterality of the extremities, to adapt the ankle splint of the present invention for the right or left extremity. However, the adjustability of the straps and compressibility of the inner layer of foam allows a single size splint to fit a range of sizes of lower extremities so that while a plurality of sizes of splints must be made to fit the entire population, it is not necessary to customize each splint to a particular patient but rather one size splint will fit a range of patients.

In summary, therefore, a multimembered splint for placement upon the lower extremity and foot of a patient to immobilize the ankle joint of the patient in the process of treatment of an ankle sprain includes four members that surround the lower extremity and foot and are held in place by adjustable straps. The members conform anatomically to the characteristics of the lower extremity including a flare in the lateral and medial members to accommodate the natural flare of the leg and recesses in the lateral and medial members where they fit over the lateral and medial malleoli so as to reduce pressure upon the bony prominence of the malleoli but apply greater pressure to the peri-malleolar tissues to reduce edema and prevent pressure sores. While a preferred embodiment of the invention is described and illustrated herein, it will be understood by those of ordinary skill in the art and others, that several changes can be made to the illustrated embodiment while remaining within the spirit and scope of the present invention. For example, a wide variety of materials can be used in the manufacture of the splint as long as the rigidity of the members is maintained. Further, while hook and loop fastening straps of the Velcro type have been described, other fastening straps are possible. The dimensions given herein are exemplary only and are not intended to limit the scope of the invention. The invention, therefore, should be defined solely by reference to the appended claims.

The embodiments of the invention in which an exclusive property or privilege is claimed are as follows:

1. A walking splint removably attachable to the lower leg and foot to substantially immobilize the ankle joint comprising:
   a discrete posterior member of substantially rigid material, inflexible at the ankle joint and adapted for placement on the back of said leg, said posterior member extending from the midpoint of the calf of said leg downwardly around the heel of said foot and underlying the bottom of said foot to insure a constant right angular relationship between said leg and said foot;
   a discrete anterior member of substantially rigid material adapted for placement on the front of said leg, said anterior member extending from a point substantially at the same height as an upper end of said posterior member, said anterior member overlying at least a portion of said foot;
   a discrete lateral member of substantially rigid material adapted for placement over the lateral portion of said leg and extending to cover the lateral malleolus, said lateral member having a distal outward flare in the portion covering the malleolus and including a recess formed in the distal portion to anatomically conform to the lateral malleolus;
   a discrete medial member of substantially rigid material adapted for placement over the medial portion of said leg and extending to cover the medial malleolus, said medial malleolus being covered by a distal portion of said medial member which is flared outwardly with respect to the remaining portion of said medial member and including a recess formed in the distal portion covering said malleolus of a size adapted to anatomically conform to the medial malleolus;
   a plurality of straps vertically spaced from one another along said posterior member, said straps being operable to encircle said members and to tighten to apply tension to hold said members firmly against said leg and said foot, said straps including a means for fastening said straps.

2. The walking splint of claim 1, wherein said posterior member includes a plurality of slots integrally formed in the posterior member, said straps passing through said slots, said straps having attached at one end thereof a rectangular ring of a size larger then the slots formed in said posterior member.

3. The splint of claim 1, wherein said posterior, anterior, lateral and medial members are each lined with a compressible material interposed between the respective member and the leg and foot over which said member lies, said compressible material being of a thickness adapted to provide a close fit of said splint on said leg and foot at the same time providing more comfort for individual anatomic variations of said leg and foot from patient to patient.

4. The splint of claim 3, wherein said compressible material is so molded in said recessed portions of said medial and lateral members such as to conform to the anatomical configuration of the bony, medial and lateral malleolar prominences so that less pressure is applied over said prominences and more pressure is applied over the peri-malleolar soft tissue.

5. The splint of claim 4, wherein said anterior member extends to cover a portion of the dorsum of the foot but not to overlie the metatarsophalangeal joints.

6. The splint of claim 5, wherein said portion of said posterior member underlying said foot includes an integral arch support formed therein to accommodate the arch of the foot.

7. The splint of claim 6, wherein said arch support is formed to respectively accommodate either the right or left foot of a patient.

8. The splint of claim 5, wherein said recessed portion of said medial member is larger than said recessed portion of said lateral member.

9. The splint of claim 5, wherein the exterior surface of the portion of said posterior member underlying said foot comprises an antiskid surface.

10. The splint of claim 9, wherein said posterior member includes an antiskid material affixed to the exterior of the undersurface of said portion of said posterior member underlying said foot.

11. The splint of claim 9, wherein said antiskid surface is integrally formed in said posterior member.

12. The splint of claim 5, wherein said retaining slots in said posterior member prevent longitudinal movement of said fastener straps.

13. The splint of claim 5, wherein said lateral, medial and anterior members have fastening strips attached respectively to each of them, said fastening strips cooperating with said straps to hold said lateral, medial and anterior members in position longitudinally on said lower extremity.

* * * * *